(12) United States Patent
Li et al.

(10) Patent No.: US 12,144,638 B2
(45) Date of Patent: Nov. 19, 2024

(54) METHODS AND DEVICES OF GENERATING PREDICTED BRAIN IMAGES

(71) Applicant: TAIPEI MEDICAL UNIVERSITY, Taipei (TW)

(72) Inventors: Yi-Tien Li, Taipei (TW); Cheng-Yu Chen, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 177 days.

(21) Appl. No.: 17/895,036

(22) Filed: Aug. 24, 2022

(65) Prior Publication Data

US 2024/0065609 A1 Feb. 29, 2024

(51) Int. Cl.
*A61B 5/00* (2006.01)
*A61B 5/055* (2006.01)
*A61B 5/103* (2006.01)

(52) U.S. Cl.
CPC ............ *A61B 5/4064* (2013.01); *A61B 5/055* (2013.01); *A61B 5/103* (2013.01); *A61B 5/742* (2013.01)

(58) Field of Classification Search
None
See application file for complete search history.

(56) References Cited

U.S. PATENT DOCUMENTS

| 2019/0156200 A1 | 5/2019 | Hu |
| 2019/0332900 A1 | 10/2019 | Sjolund et al. |
| 2019/0355439 A1* | 11/2019 | Murray ................. G16B 25/10 |
| 2022/0028139 A1 | 1/2022 | Mitra et al. |
| 2022/0319675 A1* | 10/2022 | Mork ................... G06N 3/0464 |
| 2023/0097895 A1* | 3/2023 | Lou ........................... G06T 7/11 |
| | | 382/131 |

(Continued)

FOREIGN PATENT DOCUMENTS

| CN | 112353381 A | * 2/2021 | ........... A61B 5/0035 |
| CN | 113724880 A | * 11/2021 | |
| KR | 102472550 B1 | 11/2022 | |
| TW | 202209349 A | 3/2022 | |

(Continued)

OTHER PUBLICATIONS

Seo et al., "Learning Deeply Enriched Representations of Longitudinal Imaging-Genetic Data to Predict Alzheimer's Disease Progression," (Dec. 9-12, 2021). 2021 IEEE International Conference on Bioinformatics and Biomedicine (BIBM), Houston, TX, USA, 2021, pp. 732-735. (Year: 2021).*

(Continued)

*Primary Examiner* — Joel Lamprecht
*Assistant Examiner* — Ashish S Jasani
(74) *Attorney, Agent, or Firm* — Idea Intellectual Limited; Margaret A. Burke; Sam T. Yip

(57) ABSTRACT

Disclosed are methods and devices of generating predicted brain images. The present disclosure provides a method of generating a predicted brain image. The method comprises: receiving a first brain image; encoding the first brain image to generate a latent vector; and decoding the latent vector and one or more conditional features to generate the predicted brain image. The first brain image is generated by a magnetic resonance imaging (MRI) method. The one or more conditional features include at least one of: an age in future, a gender, previous brain images, omics features, and medical history. The latent vector is multiplied by a first normal distribution.

18 Claims, 20 Drawing Sheets

(56) References Cited

U.S. PATENT DOCUMENTS

2023/0334657 A1* 10/2023 Kim .................. G06T 7/0012

FOREIGN PATENT DOCUMENTS

| TW | 202223917 A | 6/2022 |
|---|---|---|
| TW | I807972 B | 7/2023 |
| WO | 2022138960 A1 | 6/2022 |

OTHER PUBLICATIONS

Wang et al., "Grant Report on PREDICT-ADFTD: Multimodal Imaging Prediction of AD/FTD and Differential Diagnosis," (Oct. 30, 2019), J Psychiatry Brain Sci. 2019;4:e190017. (Year: 2019).*

Lei et al., "Predicting clinical scores for Alzheimer's disease based on joint and deep learning," Expert Systems With Applications, 187, (2022), 115966. (Year: 2022).*

Zhou et al., "Latent Representation Learning for Alzheimer's Disease Diagnosis With Incomplete Multi-Modality Neuroimaging and Genetic Data," (Oct. 2019), IEEE Transactions on Medical Imaging, vol. 38, No. 10, 2411-2422. (Year: 2019).*

Lee et al., "Predicting Alzheimer's disease progression using multimodal deep learning approach," (Feb. 13, 2019), Scientific Reports, (2019) 9:1952. (Year: 2019).*

Lin et al., "Deep Learning with Neuroimaging and Genomics in Alzheimer's Disease," (Jul. 24, 2021), Int. J. Mol. Sci.2021, 22, 7911. (Year: 2021).*

Kilian Hetta et al., "Multi-scale Graph-based Grading for Alzheimer's Disease Prediction", Medical Image Analysis, 2020, Elsevier.

International Search Report and Written Opinion of corresponding PCT Patent Application No. PCT/US2023/071163 mailed on Nov. 29, 2023.

Office Action of corresponding Taiwan patent application No. 111131880 mailed on Jan. 6, 2024.

* cited by examiner

METHODS AND DEVICES OF GENERATING PREDICTED BRAIN IMAGES

FIELD OF THE INVENTION

The present disclosure relates to a method of generating predicted brain images and related devices. In particular, the present disclosure relates to methods of generating predicted brain images based on a current brain image and estimating dementia risk based on predicted brain images and the related devices.

BACKGROUND

Medical advances and declining birthrates have accelerated the aging of society in Taiwan. The number of dementia patients has increased year by year. Based on an investigation of Taiwan Alzheimer Disease Association (commissioned by the Ministry of Health and Welfare of Taiwan) and the demographic data at the end of December 2019 from the Ministry of the Interior of Taiwan, 1 in 12 people over the age of 65 have dementia, and 1 in 5 people over the age of 80 have dementia. Beyond Taiwan, populations in developing and developed countries around the world are facing aging populations. Therefore, brain degeneration research will undeniably become increasingly important going into the future.

SUMMARY OF THE INVENTION

Since Taiwan is an aging society, the development of early detection indicators and risk prediction models for brain degeneration would be a first step for immediate intervention, delaying disease progression, and reducing the cost of social medical care.

The present disclosure can predict the brain conditions and output one or more predicted brain images based on one or more current brain images. In addition to the one or more current brain images, the age in future, gender, one or more previous brain images, omics features, and medical history would be also used to facilitate the prediction. The one or more predicted brain images would also facilitate determination of a predicted clinical dementia rating-sum of boxes (CDR-SB) score and dementia subtype.

An embodiment of the present disclosure provides a method of generating a predicted brain image. The method comprises: receiving a first brain image; encoding the first brain image to generate a latent vector; and decoding the latent vector and one or more conditional features to generate the predicted brain image. The first brain image is generated by a magnetic resonance imaging (MRI) method. The one or more conditional features include at least one of: an age in future, a gender, previous brain images, omics features, and medical history. The latent vector is multiplied by a first normal distribution.

Another embodiment of the present disclosure provides a device for generating a predicted brain image. The device comprises a processor and a memory coupled with the processor. The processor executes computer-readable instructions stored in the memory to perform operations. The operations comprise: receiving a first brain image; by means of the processor, encoding the first brain image to generate a latent vector; and by means of the processor, decoding the latent vector and one or more conditional features to generate the predicted brain image. The first brain image is generated by a magnetic resonance imaging (MRI) method. The one or more conditional features include at least one of: an age in future, a gender, previous brain images, omics features, and medical history. The latent vector is multiplied by a first normal distribution.

BRIEF DESCRIPTION OF THE DRAWINGS

In order to describe the manner in which advantages and features of the present disclosure can be obtained, a description of the present disclosure is rendered by reference to specific embodiments thereof, which are illustrated in the appended drawings. These drawings depict only example embodiments of the present disclosure and are not therefore to be considered limiting its scope.

DETAILED DESCRIPTION

Figure 1:
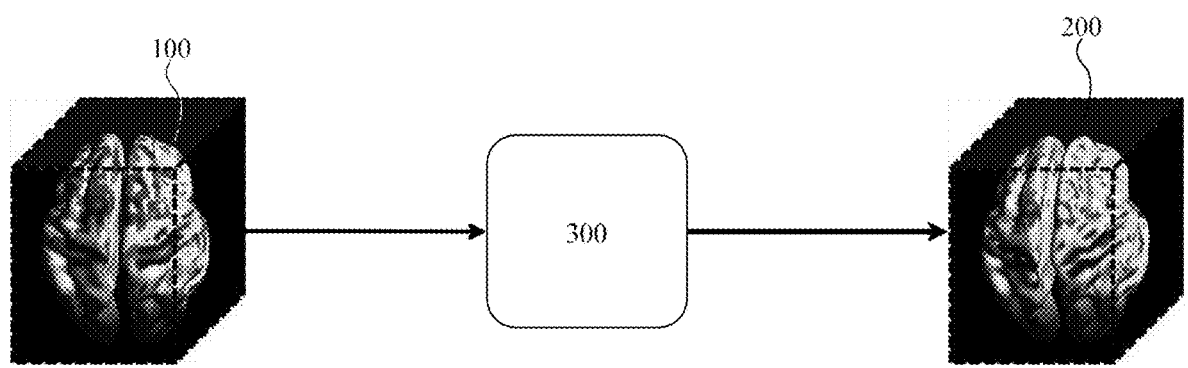
FIG. 1 illustrates a diagram of generating one or more predicted brain images according to some embodiments of the present disclosure.

The following disclosure provides many different embodiments, or examples, for implementing different features of the provided subject matter. Specific examples of operations, components, and arrangements are described below to simplify the present disclosure. These are, of course, merely examples and are not intended to be limiting. For example, a first operation performed before or after a second operation in the description may include embodiments in which the first and second operations are performed together, and may also include embodiments in which additional operations may be performed between the first and second operations. For example, the formation of a first feature over, on or in a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Time relative terms, such as "prior to," "before," "posterior to," "after" and the like, may be used herein for ease of description to describe the relationship of one operation or feature to another operation(s) or feature(s) as illustrated in the figures. The time relative terms are intended to encompass different sequences of the operations depicted in the figures. Further, spatially relative terms, such as "beneath," "below," "lower," "above," "upper" and the like, may be used herein for ease of description to describe the relationship of one element or feature to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. Relative terms for connections, such as "connect," "connected," "connection," "couple," "coupled," "in communication," and the like, may be used herein for ease of description to describe an operational connection, coupling, or linking one between two elements or features. The relative terms for connections are intended to encompass different connections, coupling, or linking of the devices or components. The devices or components may be directly or indirectly connected, coupled, or linked to one another through, for example, another set of components. The devices or components may be wired and/or wirelessly connected, coupled, or linked with each other.

As used herein, the singular terms "a," "an," and "the" may include plural referents unless the context clearly indicates otherwise. For example, reference to a device may include multiple devices unless the context clearly indicates otherwise. The terms "comprising" and "including" may indicate the existences of the described features, integers, steps, operations, elements, and/or components, but may not exclude the existences of combinations of one or more of the features, integers, steps, operations, elements, and/or components. The term "and/or" may include any or all combinations of one or more listed items.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

The nature and use of the embodiments are discussed in detail as follows. It should be appreciated, however, that the present disclosure provides many applicable inventive concepts that can be embodied in a wide variety of specific contexts. The specific embodiments discussed are merely illustrative of specific ways to embody and use the disclosure, without limiting the scope thereof.

The present disclosure takes advantage of several databases, including the public database of the Alzheimer's Disease Neuroimaging Initiative (ADNI) of the US, Neuroimaging in Frontotemporal Dementia (NIFD), and Japan ANDI (J-ANDI). The data in the databases may include the $^{18}$F-fluorodeoxyglucose positron emission tomography (18 FDG-PET) data, amyloid positron emission tomography (PET) data, magnetic resonance imaging (MRI) data, and clinical diagnoses of cognitive normal (CN) subjects, of mild cognitive impairment (MCI) subjects, of Alzheimer's disease (or Alzheimer's dementia) (AD) patients, and of frontal temporal dementia (FTD) patients, in which these subjects and patients have been tracked for three years or more. The numbers of cases from different databases are shown in Table 1.

TABLE 1

|  | ADNI | NIFD | J-ADNI |
| --- | --- | --- | --- |
| CN | 3130 | 148 | 729 |
| MCI | 3125 | 231 | 1242 |
| AD | 2507 |  | 546 |
| FTD |  | 698 |  |

The present disclosure further establishes an automated analysis platform for radiomics so as to locate one or more biomarkers that influence healthy aging in early radiomics data. Furthermore, a personal healthy aging diagram prediction model and dementia subtype early determination model can be established.

The patients' data may further include 2,060 healthy/sub-healthy subjects from three sub-plans. The first sub-plan may include 120 MCI patients, 60 mild behavioral impairment (MBI) patients, 120 healthy subjects. The second sub-plan may include 960 healthy/sub-healthy subjects without dementia. The third sub-plan may include 800 sub-healthy subjects, which may be cognitively unimpaired (CU), subjective cognitive decline (SCD), MCI, or all cause prodromal dementia.

The patients' data may further include 1,160 patients drawn from confirmed cases of dementia subtypes. The 1,160 patients may include 500 patients with vascular dementia (VaD), 240 patients with Alzheimer's disease (or Alzheimer's dementia) (AD), 240 patients with Parkinson disease (PD), 120 patients with dementia with Lewy bodies (DLB), and 60 patients with frontotemporal dementia (FTD).

FIG. 1 illustrates a diagram of generating one or more predicted brain images according to some embodiments of the present disclosure. An image generation procedure 300 may receive one or more brain images 100. The one or more brain images 100 may be imaged by an 18 FDG-PET method, a PET method, or an MRI method. The one or more brain images 100 may be made of pixels or voxels (e.g., volume pixels).

Upon receipt of the one or more brain images 100, the image generation procedure 300 may correspondingly generate and output the one or more predicted brain images 200. When the inputted brain image 100 is generated by an 18 FDG-PET method, the predicted brain image 200 may be generated in the form of an 18 FDG-PET image. When the inputted brain image 100 is generated by a PET method, the predicted brain image 200 may be generated in the form of a PET image. When the inputted brain image 100 is generated by a MRI method, the predicted brain image 200 may be generated in the form of a MRI image.

The one or more predicted brain images 200 may be correspondingly made of pixels or voxels (e.g., volume pixels). When the inputted brain image 100 is made of pixels, the predicted brain image 200 may be made of pixels. When the inputted brain image 100 is made of voxels, the predicted brain image 200 may be made of voxels.

Figure 2:
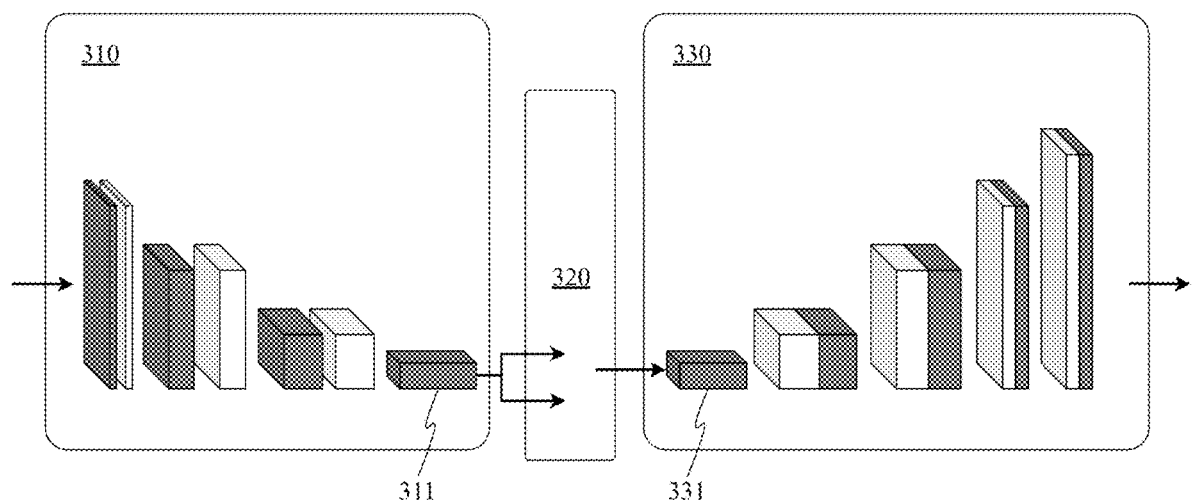
FIG. 2 illustrates a diagram of an image generation procedure according to some embodiments of the present disclosure.

FIG. 2 illustrates a diagram of an image generation procedure 300 according to some embodiments of the present disclosure. The image generation procedure 300 may include an encoder 310 and a decoder 330. A latent space 320 may be between the encoder 310 and the decoder 330.

When the image generation procedure 300 receives a brain image 100, the encoder 310 may transform or compress the brain image 100 into a low-dimensional vector 311. The brain image 100 may be transformed or compressed through a plurality of convolution calculations. After one or more convolution calculations are conducted on the brain image 100, the number of the dimensions of the brain image 100 may be reduced.

The low-dimensional vector 311 may then be transmitted to the latent space 320. In the latent space 320, the low-dimensional vector 311 may be further modified such that the desired image would be generated by the image generation procedure 300. For example, some information may be added to the low-dimensional vector 311, and the low-dimensional vector 311 would be modified. The latent space 320 may transmit a modified vector 331 to the decoder 330. The modified vector 331 may be another low-dimensional vector.

The decoder 330 may transform or recover the modified vector 331 to a high-dimensional space. The modified vector 331 may be transformed or recovered through a plurality of convolution calculations. After one or more convolution calculations to the modified vector 331, the number of the dimensions of the modified vector 331 may be increased. After the calculations of the decoder 330, the one or more predicted brain images 200 would be generated.

Figure 3:
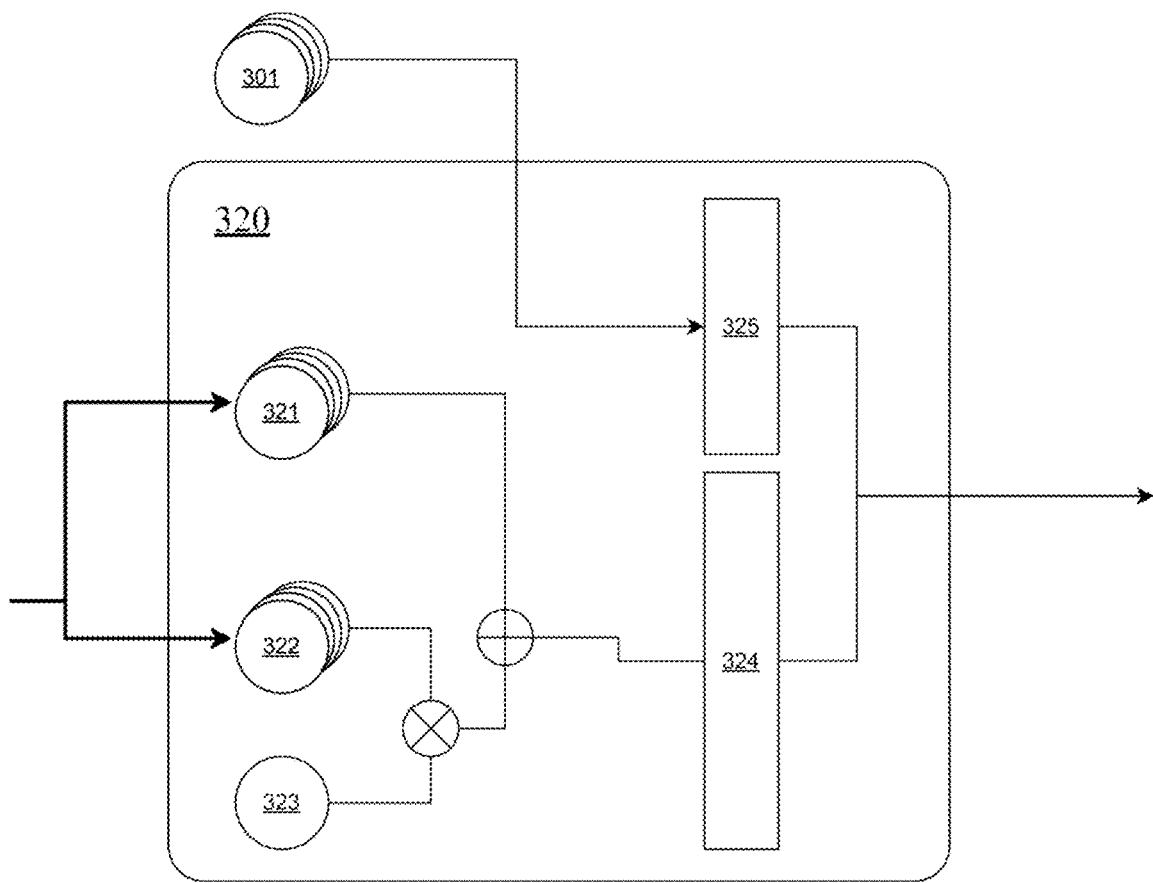
FIG. 3 illustrates a diagram of a latent space of an image generation procedure according to some embodiments of the present disclosure.

FIG. 3 illustrates a diagram of a latent space 320 of an image generation procedure 300 according to some embodiments of the present disclosure. The low-dimensional vector 311 generated in the encoder 310 may be transmitted to the latent space 320. In the latent space, the low-dimensional vector 311 may be transformed into a plurality of mean values 321 and a plurality of deviation values 322. The deviation values 322 may be multiplied with a probability distribution 323. The probability distribution may be a normal distribution in which the mean (i.e., $\mu$) equals 0 and the variance (i.e., $\sigma^2$) equals 1. The normal distribution may be represented as N~(0, 1). After the deviation values 322 are multiplied with the probability distribution, the mean values 321 and the modified deviation values (e.g., the deviation values 322 multiplied with the probability distribution) are combined and transformed to a latent vector 324. The latent vector 324 may be sampled from the normal distribution, in which the mean is 321 and the standard deviation is 322.

Some conditional features 301 may be added to the latent space. The conditional features 301 may include at least one of: the age in future to be predicted, the gender, the one or more previous brain images of the patient, the omics features of the patient, and the medical history of the patient. The omics features may include oral bacterial flora features, blood features, genomics features, and radiomics features. These omics features may be omics biomarkers.

In some embodiments, the genomics features may include the information of whether the subject/patient has ε4 allele, ε3 allele, or ε2 allele of the Apolipoprotein E (APOE) gene. The genomics features may include the information of whether the tau proteins have defects, in which the tau proteins are produced by alternative splicing from the MAPT (microtubule-associated protein tau) gene. The genomics features may include the information of whether the granulin (GRN) gene mutants. The genomics features may include the information of whether the C9ORF72 gene mutants.

In some embodiments, the blood features may include the information of P-tau217 (phosphorylated tau at threonine-217), Aβ40 (amyloid-beta 40), and Aβ42 (amyloid-beta 42). In some embodiments, the radiomics features may include the information of brain tau PET imaging, brain amyloid PET imaging, and white matter hyperintensity imaging (with levels 0-6). In some embodiments, the medical history features may include the information of hypertension, hyperlipidemia, diabetes, and stroke.

The conditional features 301 may be transformed into a conditional vector 325. In some embodiments, the conditional vector 325 may include the elements associated with age, gender, APOE-ε4, and hypertension. For example, the element associated with the age may be calculated by [(age-50)/100] for normalizing; the element associated with the gender may be represented by 1 or 0 (e.g., male is 1, and female is 0); the element associated with the APOE-ε4 may be represented as the number of the alleles (e.g., the number of the alleles may be 0, 1, or 2); and the element associated with the hypertension may be represented by 1 or 0 (e.g., 1 is for hypertension being diagnosed, and 0 is for hypertension being not diagnosed). For example, for the 80 years old male subject who has one allele of APOE-ε4 and is diagnosed without hypertension, the corresponding conditional vector 325 may be represented as "[0.3, 1, 1, 0]."

The conditional vector 325 and the latent vector 324 are combined and then transmitted from the latent space 320. Through adding the additional features, fewer prediction errors would result. Therefore, the present disclosure can provide accurate predicted brain images and accurate prediction for CDR-SB score and dementia subtype. The present disclosure would be helpful for providing immediate intervention, delaying disease progression, and reducing the cost of social medical care.

The image generation procedure 300 may be trained by a backpropagation method. For example, in the training phase of the image generation procedure 300, the earlier brain image of a patient (e.g., the brain image obtained when the patient was 77 years old) may be input to the image generation procedure 300 as the brain image 100, and the predicted brain image 200 output from the image generation procedure 300 may be compared with the later brain image of the same patient (e.g., the brain image obtained when the patient was 80 years old). The comparison between the predicted brain image 200 and the later brain image may be represented as reconstruction loss. The reconstruction loss may be the mean square error (MSE) between the images under comparison. The reconstruction loss may be the root mean square error between the images under comparison. In some embodiments, the reconstruction loss may be the cross entropy between the images under comparison.

In some embodiments, the reconstruction loss may be calculated by the pixel-wise reconstruction loss, the region-wise reconstruction loss, and the global reconstruction loss. For example, the reconstruction loss may be a sum of different portions of the pixel-wise reconstruction loss, the region-wise reconstruction loss, and the global reconstruction loss. The pixel-wise reconstruction loss indicates the mean value calculated from the MSE values of each pixel pair between two images. The region-wise reconstruction loss indicates the MSE value calculated from the mean values of the same region of interest of two images, in which the region of interest may be one of frontal, temporal, parietal, occipital, third ventricle, thalamus, hippocampus. The global reconstruction loss indicates the MSE value calculated from the mean values of the same region of interest in the gray matter (GM) region or cerebrospinal fluid (CSF) region of two images.

Through the backpropagation method, the encoding parameters and the decoding parameters may be updated or adjusted such that the reconstruction loss is minimized. In some embodiments, the encoding parameters may be updated or adjusted first while the decoding parameters are fixed, and the decoding parameter may then be updated or adjusted while the encoding parameters are fixed. In some embodiments, the decoding parameters may be updated or adjusted first while the encoding parameters are fixed, and the encoding parameter may then be updated or adjusted while the decoding parameters are fixed. The encoding parameters may be used for encoding the brain image 100. The decoding parameters may be used for decoding the latent vector and the one or more conditional features.

Figure 4:
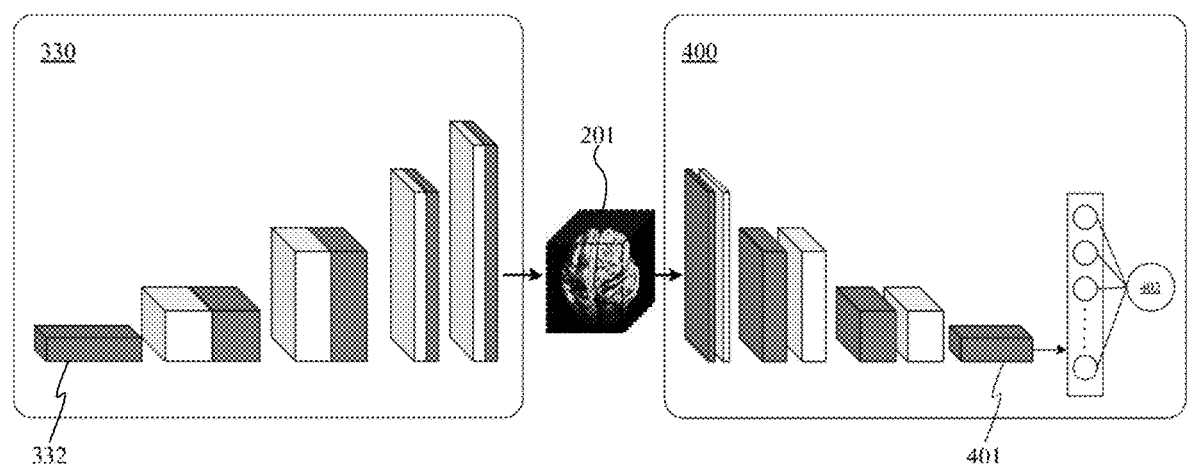
FIG. 4 illustrates a diagram of an image discrimination procedure according to some embodiments of the present disclosure.

FIG. 4 illustrates a diagram of an image discrimination procedure 400 according to some embodiments of the present disclosure. In particular, FIG. 4 illustrates interactions between the image discrimination procedure 400 and the decoder 330. In the decoder 330, a vector 332 may be transformed, recovered, or decoded to one or more brain images 201. In the decoder 330, the vector 332 may be transformed, recovered, or decoded through a plurality of convolution calculations. After one or more convolution calculations to the vector 332, the number of the dimensions of the vector 332 may be increased. After the calculations of the decoder 330, the one or more brain images 201 would be generated. In some embodiments, the decoder 330 may be called a generator.

The brain image 201 may be transmitted to the image discrimination procedure 400. When the image discrimination procedure 400 receives the brain image 201, the image discrimination procedure 400 may transform or compress the brain image 201 into a low-dimensional vector 401. The brain image 201 may be transformed or compressed through a plurality of convolution calculations. After one or more convolution calculations to the brain image 201, the number of the dimensions of the brain image 201 may be reduced. The low-dimensional vector 401 would be expanded to one or more full connected layers. Based on the one or more full connected layers, the image discrimination procedure 400 may generate a discrimination output 402. The discrimination output 402 may indicate whether the input brain image 201 is true or false.

The image discrimination procedure 400 may be trained by a backpropagation method. For example, in the training phase of the image discrimination procedure 400, the real brain image of a patient (e.g., the image which is actually imaged from a patient) may be input to the image discrimination procedure 400 as the brain image 201, and the corresponding discrimination output 402 may be output from the image discrimination procedure 400. Since the brain image input to the image discrimination procedure 400 is real, the corresponding discrimination output is supposed to be true. In contrast, if the brain image input to the image discrimination procedure 400 is fake, the corresponding discrimination output is supposed to be false. The comparison between the actual discrimination output 402 and the supposed discrimination output (which may be determined by whether the real brain image or fake brain image is input) may be represented as discriminate loss. The discriminate loss may be the mean square error. The discriminate loss may be the root mean square error. In some embodiments, the discriminate loss may be the cross entropy. Through the backpropagation method, the parameters of the image discrimination procedure 400 may be updated or adjusted such that the discriminate loss is minimized.

After the parameters of the image discrimination procedure 400 are updated or confirmed, the decoding parameters of the decoder 330 may be updated or adjusted. When the decoding parameters of the decoder 330 is trained to be updated or adjusted, the parameters of the image discrimination procedure 400 may be set to untrainable (e.g., set the variable of "trainable" equal to "false"). A vector 332 may be input to the decoder 330, and the vector 332 may be transformed, recovered, or decoded to one or more brain images 201. The one or more brain images 201 may be transmitted to the image discrimination procedure 400. Upon receipt of the one or more brain images 201, the image discrimination procedure 400 may output the discrimination output 402 accordingly. The comparison between the discrimination output 402 and the supposed discrimination output (which may be determined by whether the brain image 201 is real or fake) may be represented as discriminate loss. The discriminate loss may be the mean square error. The discriminate loss may be the root mean square error. In some embodiments, the discriminate loss may be the cross entropy. Through the backpropagation method, the decoding parameters of the decoder 330 may be updated or adjusted such that the difference between the discriminate output of a real image and the discriminate output of a generated (or fake) image is minimized.

Since the decoding parameters of the decoder 330 may be updated or adjusted based on both the reconstruction loss and the discriminate loss, the images generated by the decoder 330 would be more robust and reliable.

Figure 5A:
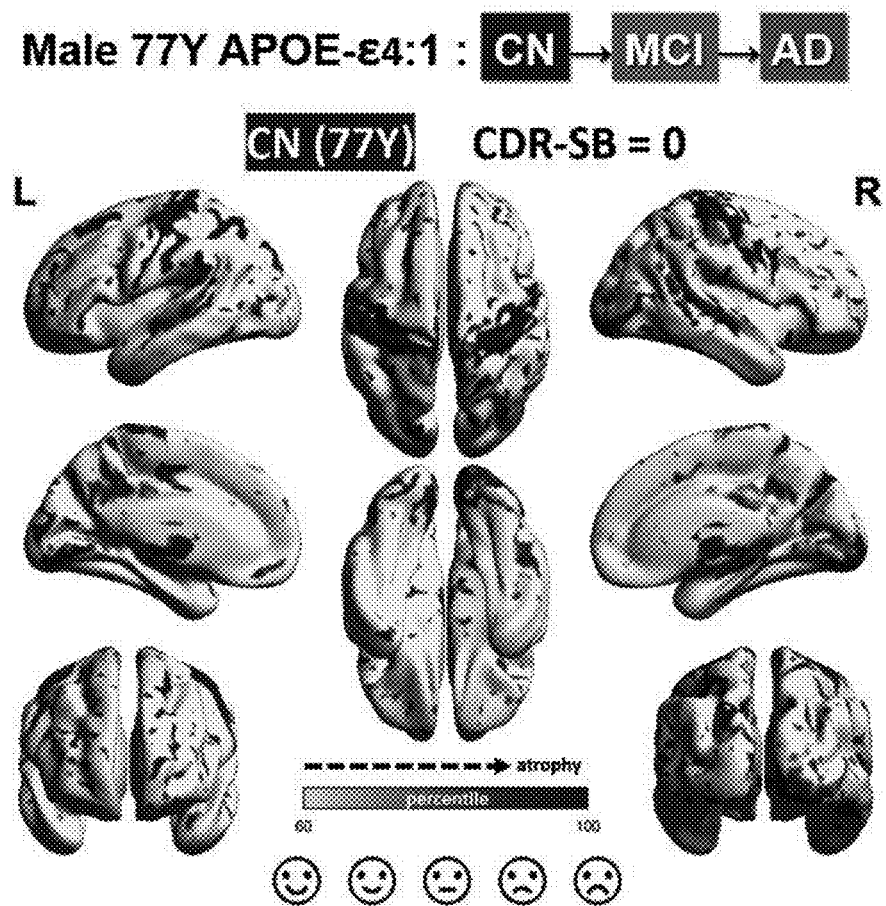
FIG. 5A shows current brain images according to some embodiments of the present disclosure.

FIG. 5A shows brain images according to some embodiments of the present disclosure. The brain images shown in FIG. 5A may be the current brain images of a given subject/patient. That is, the given subject/patient may now be 77 years old (i.e., "77Y" shown in FIG. 5A). The given subject/patient shown in FIG. 5A is male and has ε4 allele of the Apolipoprotein E (APOE) gene (i.e., "APOE-ε4:1" shown in FIG. 5A). The letters "L" and "R" in FIG. 5A indicate the left brain and the right brain, respectively. The gray or black color shown in the brain images of FIG. 5A indicates the atrophy of the cerebral cortex. The darker color shown in the brain images indicates more serious atrophy of the cerebral cortex. Based on different atrophy conditions of the brain images, the subject/patient may be determined as being cognitive normal (CN), having mild cognitive impairment (MCI), or having Alzheimer's dementia or Alzheimer's disease (AD). Based on the atrophy condition of the brain images of FIG. 5A, the subject/patient is determined as CN. Based on different atrophy conditions of the brain images, the clinical dementia rating-sum of boxes (CDR-SB) score of the subject/patient may be determined. Based on the atrophy condition of the brain images of FIG. 5A, the CDR-SB score of the subject/patient may be determined as 0. In some embodiments, the ranges of CDR-SB and the corresponding staging categories may be those shown in Table 2.

TABLE 2

| CDR-SB Range | Staging Category |
| --- | --- |
| 0 | Normal |
| 0.5-2.5 | Questionable cognitive impairment |
| 3.0-4.0 | Very mild dementia |
| 4.5-9.0 | Mild dementia |

TABLE 2-continued

| CDR-SB Range | Staging Category |
|---|---|
| 9.5-15.5 | Moderate dementia |
| 16.0-18.0 | Severe dementia |

FIGS. 5B to 5H show predicted brain images according to some embodiments of the present disclosure. The legends in FIGS. 5B to 5H may be similar or identical to those of FIG. 5A. The predicted brain images of FIGS. 5B to 5H may be generated by the image generation procedure 300 based on the current brain images shown in FIG. 5A.

Figure 5B:
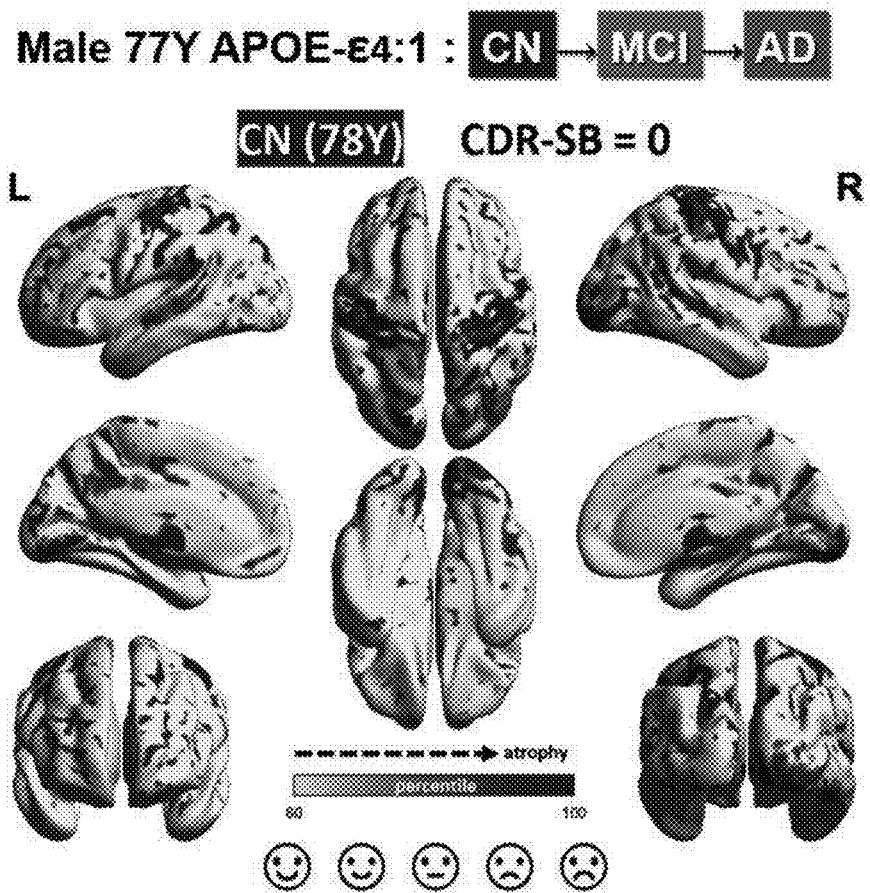
FIGS. 5B to 5H show predicted brain images according to some embodiments of the present disclosure.

FIG. 5B is the predicted brain images generated by the image generation procedure 300 based on the current brain images shown in FIG. 5A. FIG. 5B are the predicted brain images at 78 years old. Based on the atrophy condition of the predicted brain images of FIG. 5B, the subject/patient is determined as CN. Based on the atrophy condition of the predicted brain images of FIG. 5B, the CDR-SB score of the subject/patient may be determined as 0.

Figure 5C:
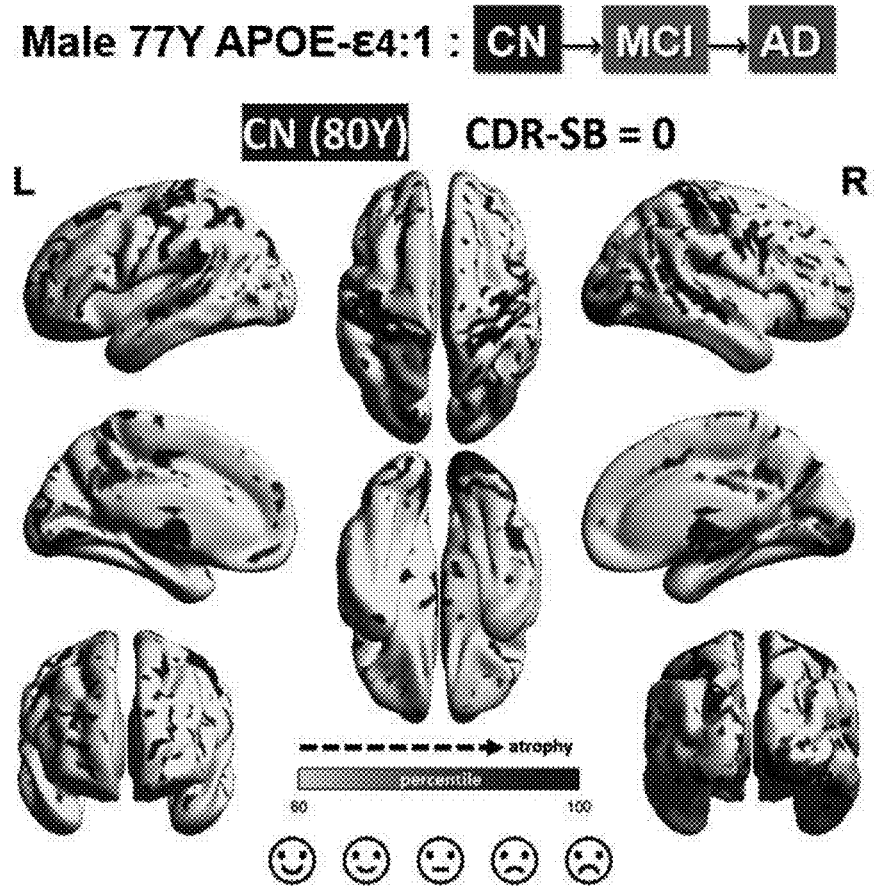

FIG. 5C is the predicted brain images generated by the image generation procedure 300 based on the current brain images shown in FIG. 5A. FIG. 5C are the predicted brain images for 80 years old. Based on the atrophy condition of the predicted brain images of FIG. 5C, the subject/patient is determined as CN. Based on the atrophy condition of the predicted brain images of FIG. 5C, the CDR-SB score of the subject/patient may be determined as 0.

Figure 5D:
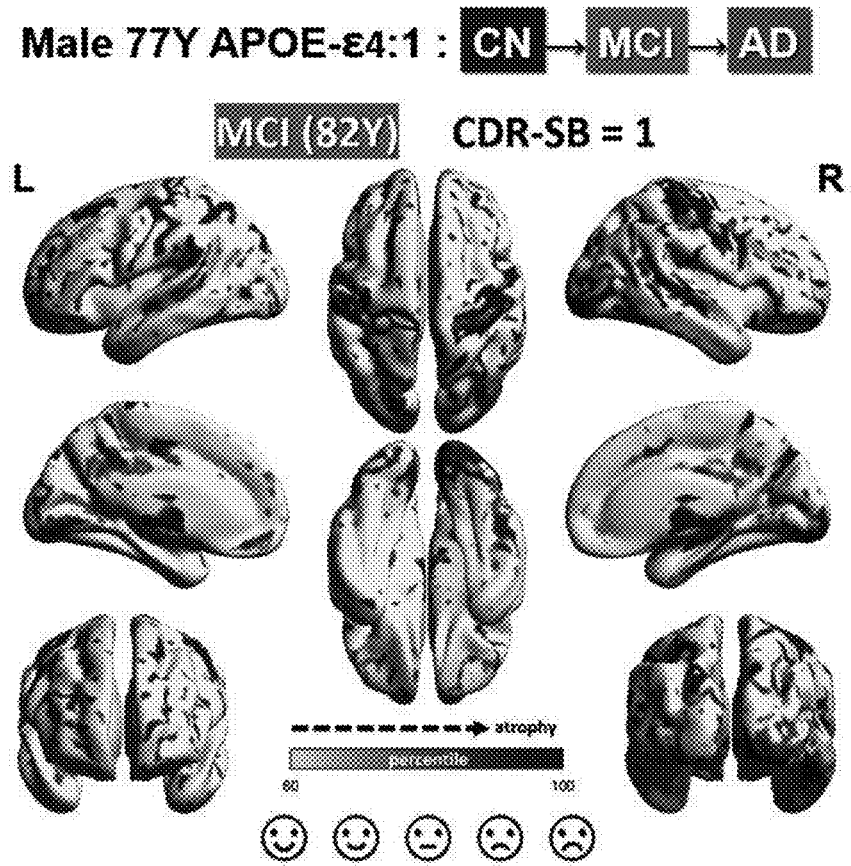

FIG. 5D is the predicted brain images generated by the image generation procedure 300 based on the current brain images shown in FIG. 5A. FIG. 5D are the predicted brain images for 82 years old. Based on the atrophy condition of the predicted brain images of FIG. 5D, the subject/patient is determined as MCI. Based on the atrophy condition of the predicted brain images of FIG. 5D, the CDR-SB score of the subject/patient may be determined as 1.

Figure 5E:
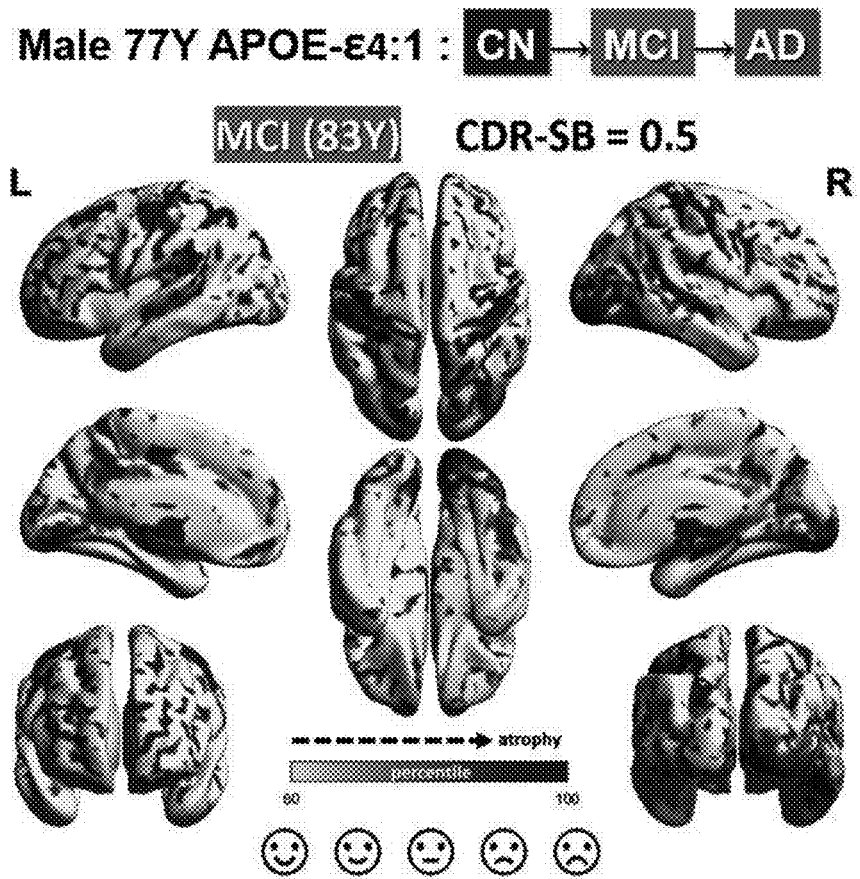

FIG. 5E is the predicted brain images generated by the image generation procedure 300 based on the current brain images shown in FIG. 5A. FIG. 5E are the predicted brain images for 83 years old. Based on the atrophy condition of the predicted brain images of FIG. 5E, the subject/patient is determined as MCI. Based on the atrophy condition of the predicted brain images of FIG. 5E, the CDR-SB score of the subject/patient may be determined as 0.5. The similarity of the CDR-SB scores in FIGS. 5D and 5E may indicate that the atrophy conditions for 82-year old and 83-year old may vary slightly.

Figure 5F:
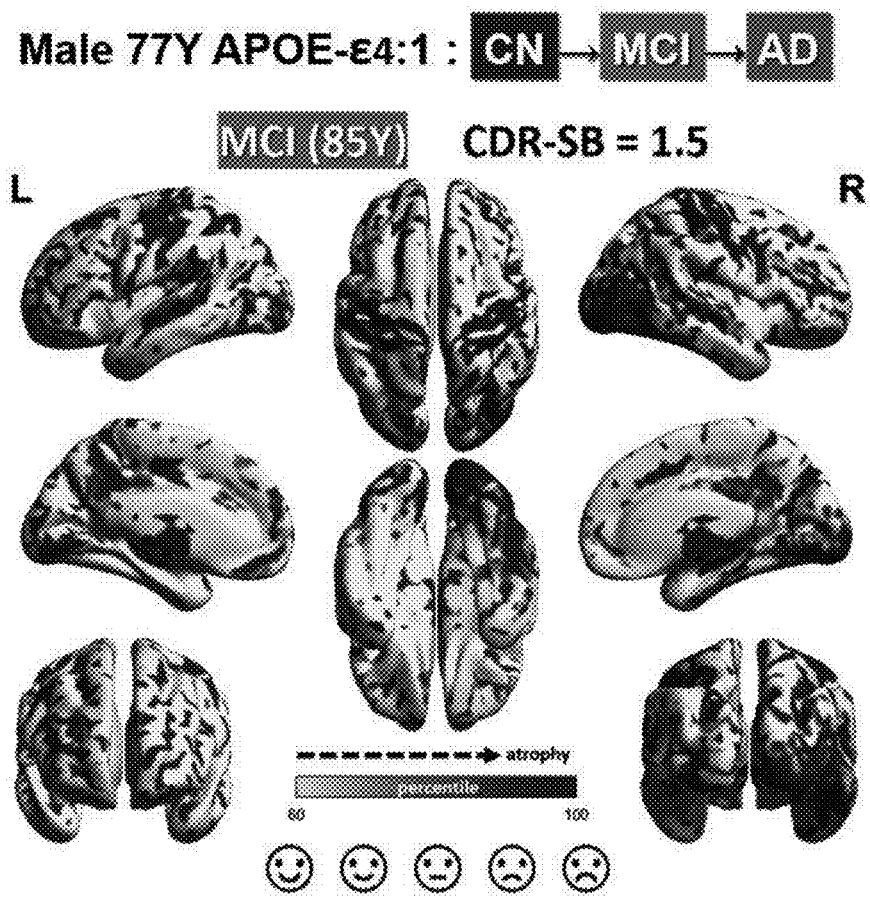

FIG. 5F is the predicted brain images generated by the image generation procedure 300 based on the current brain images shown in FIG. 5A. FIG. 5F are the predicted brain images for 85 years old. Based on the atrophy condition of the predicted brain images of FIG. 5F, the subject/patient is determined as MCI. Based on the atrophy condition of the predicted brain images of FIG. 5F, the CDR-SB score of the subject/patient may be determined as 1.5.

Figure 5G:
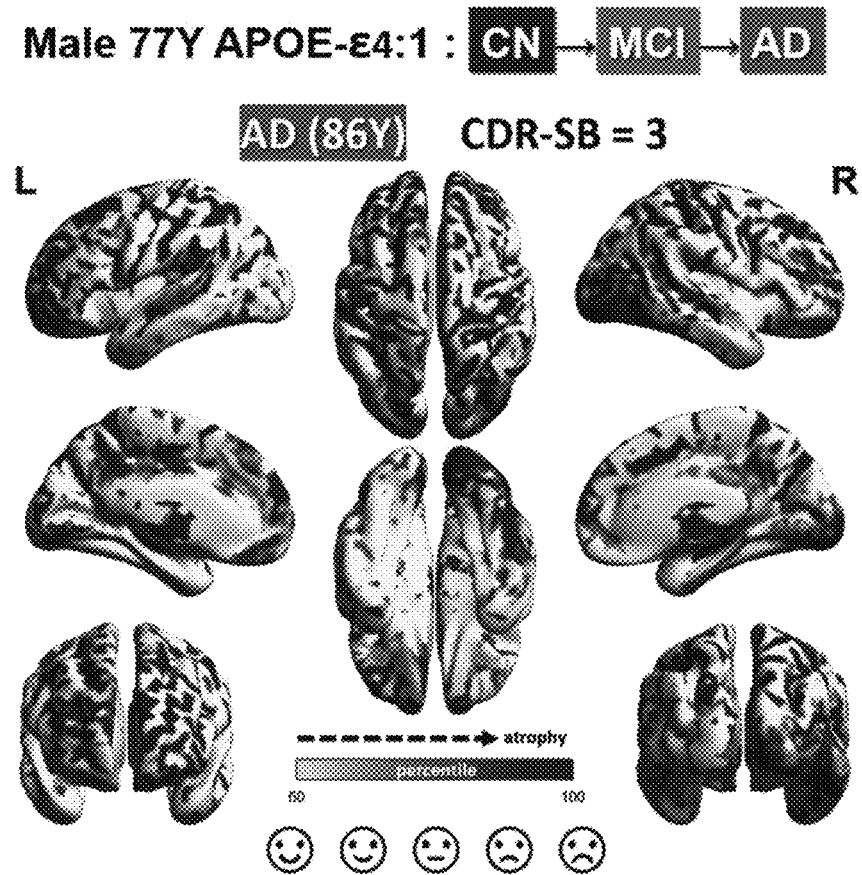

FIG. 5G is the predicted brain images generated by the image generation procedure 300 based on the current brain images shown in FIG. 5A. FIG. 5G are the predicted brain images for 86 years old. Based on the atrophy condition of the predicted brain images of FIG. 5G, the subject/patient is determined as AD. Based on the atrophy condition of the predicted brain images of FIG. 5G, the CDR-SB score of the subject/patient may be determined as 3.

Figure 5H:
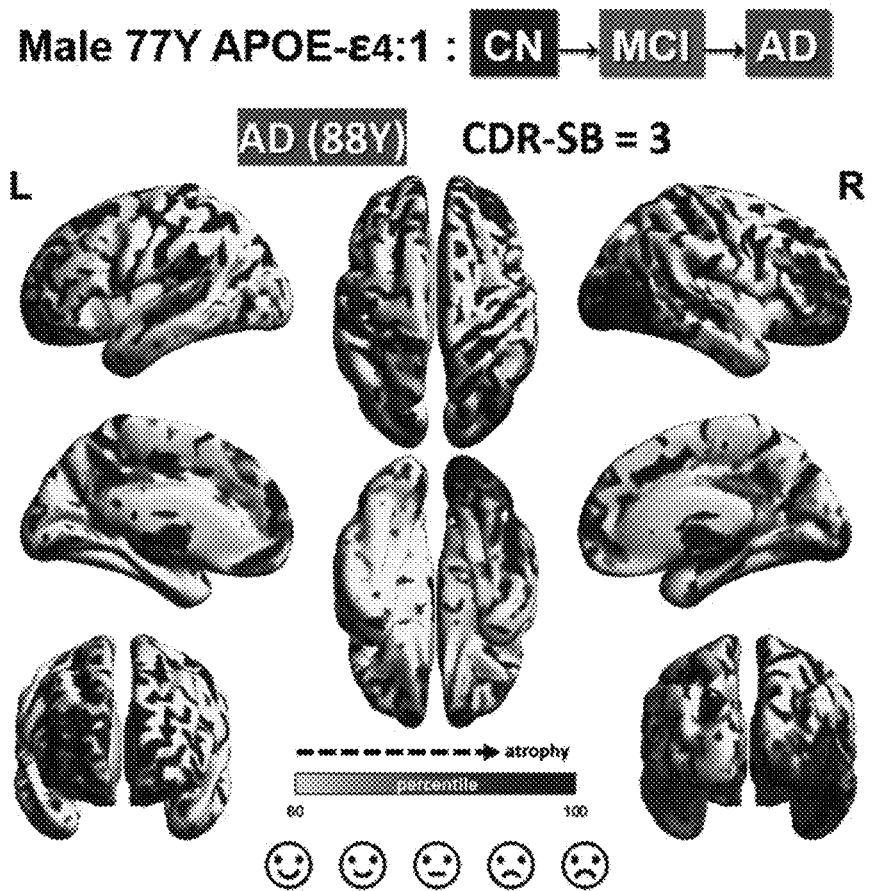

FIG. 5H is the predicted brain images generated by the image generation procedure 300 based on the current brain images shown in FIG. 5A. FIG. 5H are the predicted brain images for 88 years old. Based on the atrophy condition of the predicted brain images of FIG. 5H, the subject/patient is determined as AD. Based on the atrophy condition of the predicted brain images of FIG. 5H, the CDR-SB score of the subject/patient may be determined as 3.

Figure 6A:
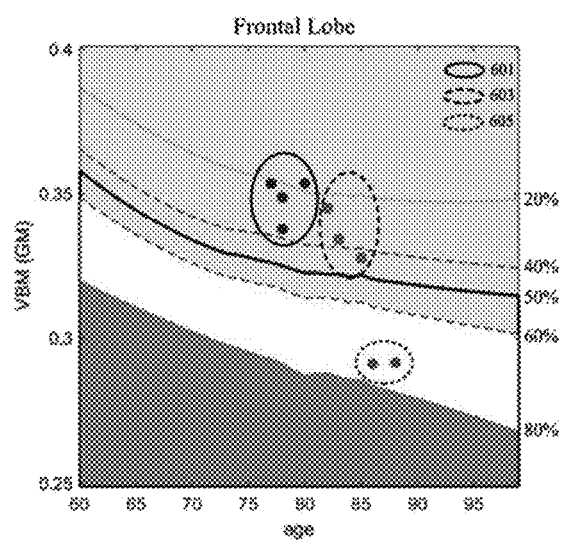
FIGS. 6A to 6D illustrate diagrams of voxel-based morphometry according to some embodiments of the present disclosure.
Figure 6B:
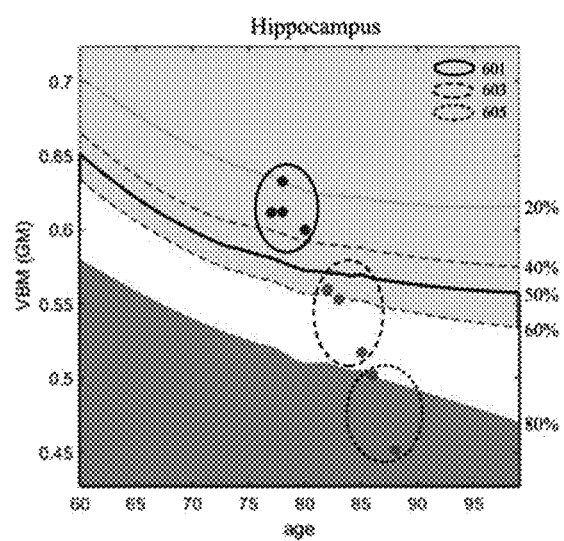
Figure 6C:
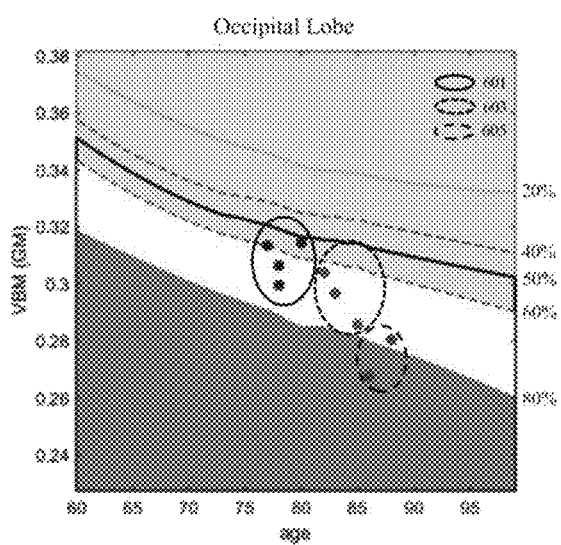
Figure 6D:
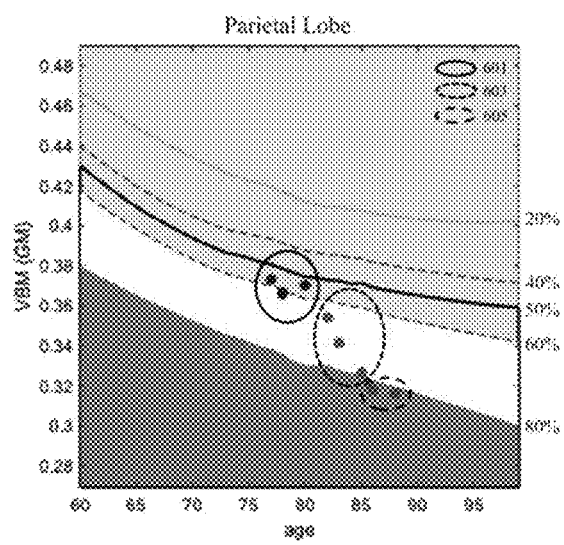

FIGS. 6A to 6D illustrate diagrams of voxel-based morphometry (VBM) according to some embodiments of the present disclosure. In particular, FIGS. 6A to 6D illustrate diagrams of VBM results of the gray matter (GM) in different portions of the brain. FIG. 6A shows the VBM result of the GM in the frontal lobe. FIG. 6B shows the VBM result of the GM in the hippocampus. FIG. 6C shows the VBM result of the GM in the occipital lobe. FIG. 6D shows the VBM result of the GM in the parietal lobe.

The x-axis in FIGS. 6A to 6D indicates the age. The y-axis in FIGS. 6A to 6D indicates the VBM value of GM. In FIGS. 6A to 6D, the percentile lines of 20%, 40%, 60%, and 80% for the VBM value are illustrated. In FIGS. 6A to 6D, the points in the circles 601 may correspond to the conditions determined as CN. In FIGS. 6A to 6D, the points in the circles 603 may correspond to the conditions determined as MCI. In FIGS. 6A to 6D, the points in the circles 605 may correspond to the conditions determined as AD. The less VMB value may indicate the more serious atrophy of the GM. In each of FIGS. 6A to 6D, the youngest point (i.e., the left-most point) may be calculated from one or more real brain images, and the other points may be calculated from one or more predicted brain images.

Figure 7:
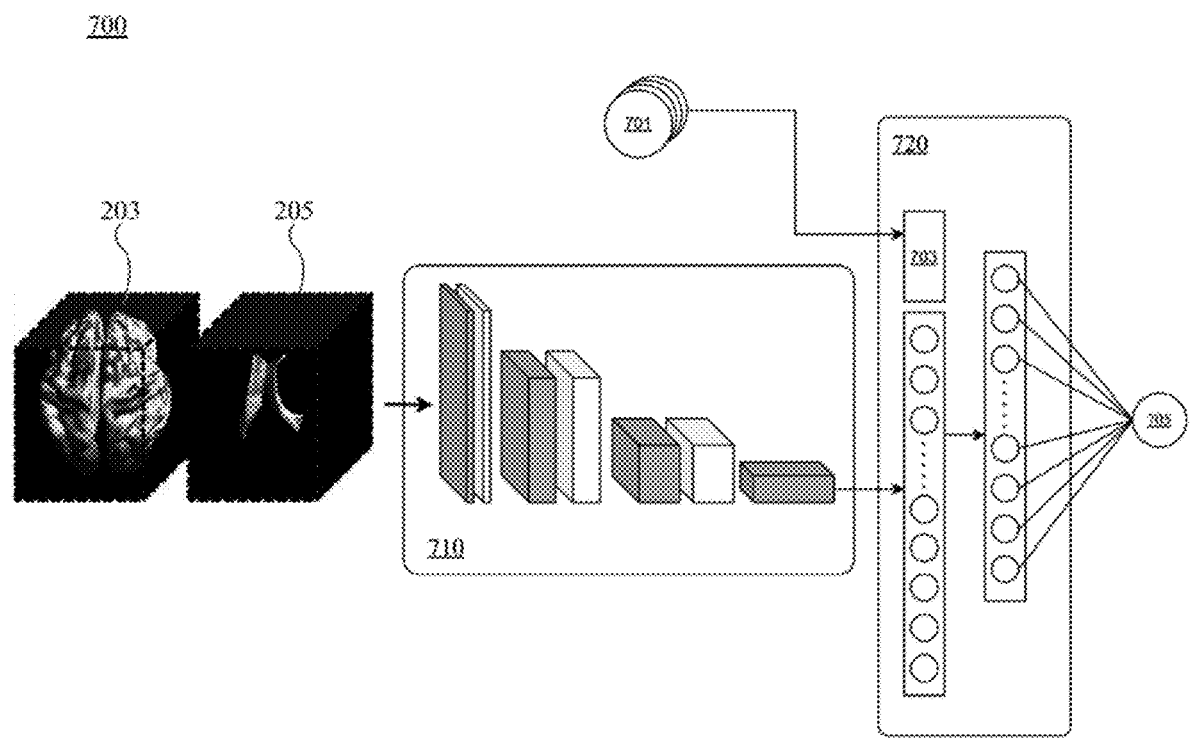
FIG. 7 illustrates a diagram of determining a clinical dementia rating-sum of boxes (CDR-SB) score according to some embodiments of the present disclosure.

FIG. 7 illustrates a diagram of determining a clinical dementia rating-sum of boxes (CDR-SB) score according to some embodiments of the present disclosure. Procedure 700 may be used to determine a CDR-SB score. In procedure 700, one or more brain images may be input. The input brain images may be real brain images (e.g., the brain images 100 which are actually imaged from a subject/patient). The input brain images may be predicted brain images (e.g., the brain images 200 which is generated by the image generation procedure 300). In some embodiments, some specific components or segmentations of the brain images may be input. For example, one or more gray matter (GM) images 203 and one or more cerebrospinal fluid (CSF) images 205 may be input. The one or more GM images 203 and the one or more CSF images 205 may be segmented from the real brain images or the predicted brain images.

In some embodiments, one GM image 203 and one CSF image 205 may be input to a convolution neural network (CNN) 710. The CNN 710 may be a ResNet. In some embodiments, the CNN 710 may be a modified ResNet.

In some embodiments, the modified ResNet for the CNN 710 includes several convolution layers. Each convolution layer indicates a convolution calculation to the input data, and the output data is generated upon the convolution calculation. The first half of the convolution layers of this modified ResNet may be dilated convolution layers, and the second half of the the convolution layers of this modified ResNet may be normal convolution layers. Each dilated convolution layer is capable to increase the receptive field of the input data, and each normal convolution layer is capable to decrease the receptive field of the input data. For each dilated convolution layer of this modified ResNet, the input data skip concatenates to the output data so as to preserve the details in high frequency. For example, the skip concatenating may be carried out by adding the input data to the output data pixel-by-pixel. For the first normal convolution layer in the second half of the convolution layers of this modified ResNet, the input data skip concatenates to the output data so as to preserve the details in high frequency.

When the CNN 710 receives the GM image 203 and the CSF image 205, the CNN 710 may transform or compress the GM image 203 and the CSF image 205 into a low-dimensional vector. The GM image 203 and the CSF image 205 may be transformed or compressed through a plurality of convolution calculations. After one or more convolution calculations to the GM image 203 and the CSF image 205, the numbers of the dimensions of the GM image 203 and the CSF image 205 may be reduced.

The low-dimensional vector generated in the CNN 710 may then be transmitted to a multilayer perceptron (MLP) 720. The low-dimensional vector may be expanded in an input layer of the MLP 720 (e.g., the left-most layer in the MLP 720 shown in FIG. 7). Some conditional features 701 may be added to the input layer of the MLP 720. The MLP 720 may include several dense layers. The conditional features 701 may include at least one of: the age in future to be predicted, the gender, the one or more previous brain images of the patient, the omics features of the patient, and the medical history of the patient. The omics features may include oral bacterial flora features, blood features, genomics features, and radiomics features. These omics features may be omics biomarkers. In some embodiments, the genomics features may include the information of whether the subject/patient has ε4 allele, ε3 allele, or ε2 allele of the Apolipoprotein E (APOE) gene. The conditional features 701 may include other genomics features, blood features, radiomics features, and medical history features similar to those for the conditional features 301. In some preferred embodiments, the additional feature 701 may include the age in future and the gender.

The conditional features 701 may be transformed into a conditional vector 703. The transformation between the conditional features 701 and the conditional vector 703 may be similar to that between the conditional features 301 and the conditional vector 325. The conditional vector 703 may be combined with the input layer of the MLP 720. Through adding the additional features 701, fewer prediction errors would result. Therefore, the present disclosure can provide an accurate prediction for CDR-SB score. The present disclosure would be helpful for providing immediate intervention, delaying disease progression, and reducing the cost of social medical care.

After the calculations conducted to one or more hidden layers of the MLP 720, information in the input layer of the MLP 720 may be transformed to an output layer of the MLP 720 (e.g., the right-most layer in the MLP 720 shown in FIG. 7). Based on the information in the output layer of the MLP 720, an output 705 may be generated. The output 705 may indicate the CDR-SB score corresponding to the one or more input images (e.g., the GM image 203 and the CSF image 205).

In some embodiments, the output layer of the MLP 720 or the output 705 may indicate the respective scores of the items of the CDR table. In other embodiments, the output layer of the MLP 720 or the output 705 may indicate the types of different symptom phenotypes for FTD patients, in which the types includes BV (behavioral variant), SV (semantic variant), and PNFA (progressive non-fluent aphasia). The CDR table may include six items: "memory," "orientation," "judgment and problem solving," "community affairs," "home and hobbies," and "personal care." Therefore, the present disclosure may predict the conditions of the six items of the CDR table. In some embodiments, the CDR-SB may be the sum of the scores of the six items.

The CNN 710 and the MLP 720 may be trained based on a plurality of known cases. For example, in each known case, the input GM image 203 and the input CSF image 205, the corresponding CDR-SB score, and the corresponding score of the six items of the CDR table are known. The CNN 710 and the MLP 720 may be trained through a backpropagation method. That is, the parameters of the CNN 710 and the MLP 720 may be adjusted and updated through a backpropagation method.

Figure 8:
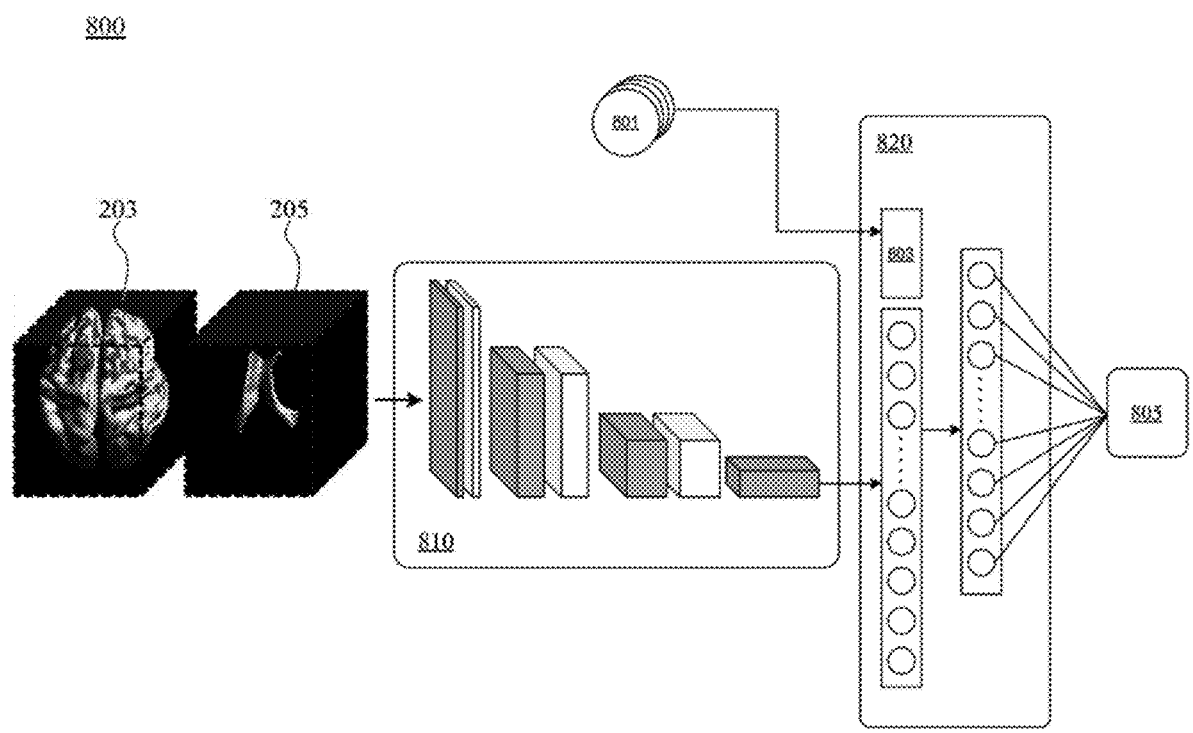
FIG. 8 illustrates a diagram of determining a dementia subtype according to some embodiments of the present disclosure.

FIG. 8 illustrates a diagram of determining a dementia subtype according to some embodiments of the present disclosure. Procedure 800 may be used to determine a dementia subtype. In procedure 800, one or more brain images may be input. The input brain images may be real brain images (e.g., the brain images 100 which are actually imaged from a subject/patient). The input brain images may be predicted brain images (e.g., the brain images 200 which is generated by the image generation procedure 300). In some embodiments, some specific components or segmentations of the brain images may be input. For example, one or more gray matter (GM) images 203 and one or more cerebrospinal fluid (CSF) images 205 may be input. The one or more GM images 203 and the one or more CSF images 205 may be segmented from the real brain images or the predicted brain images.

In some embodiments, one GM image 203 and one CSF image 205 may be input to a convolution neural network (CNN) 810. The CNN 810 may be a ResNet. In some embodiments, the CNN 810 may be a modified ResNet.

In some embodiments, the modified ResNet for the CNN 810 includes several convolution layers. Each convolution layer indicates a convolution calculation to the input data, and the output data is generated upon the convolution calculation. For first two-thirds convolution layers in this modified ResNet, the input data skip concatenates to the output data so as to preserve the details in high frequency. For example, the skip concatenating may be carried out by adding the input data to the output data pixel-by-pixel.

When the CNN 810 receives the GM image 203 and the CSF image 205, the CNN 810 may transform or compress the GM image 203 and the CSF image 205 into a low-dimensional vector. The GM image 203 and the CSF image 205 may be transformed or compressed through a plurality of convolution calculations. After one or more convolution calculations on the GM image 203 and the CSF image 205, the numbers of the dimensions of the GM image 203 and the CSF image 205 may be reduced.

The low-dimensional vector generated in the CNN 810 may then be transmitted to a multilayer perceptron (MLP) 820. The low-dimensional vector may be expanded in an input layer of the MLP 820 (e.g., the left-most layer in the MLP 820 shown in FIG. 8). Some conditional features 801 may be added to the input layer of the MLP 820. The MLP 820 may include several dense layers. The conditional features 801 may include at least one of: the age in future to be predicted, the gender, the one or more previous brain images of the patient, the omics features of the patient, and the medical history of the patient. The omics features may include oral bacterial flora features, blood features, genomics features, and radiomics features. These omics features may be omics biomarkers. In some embodiments, the genomics features may include the information of whether the subject/patient has ε4 allele, ε3 allele, or ε2 allele of the Apolipoprotein E (APOE) gene. The conditional features 801 may include other genomics features, blood features, radiomics features, and medical history features similar to those for the conditional features 301. In some preferred embodiments, the additional feature 801 may include the omics features of the patient, and the medical history of the patient.

The conditional features 801 may be transformed into a conditional vector 803. The transformation between the conditional features 801 and the conditional vector 803 may be similar to that between the conditional features 301 and the conditional vector 325. The conditional vector 803 may be combined to the input layer of the MLP 820. Through adding the additional features 801, fewer prediction errors would result. Therefore, the present disclosure can provide an accurate prediction for dementia subtype. The present disclosure would be helpful for providing immediate intervention, delaying disease progression, and reducing the cost of social medical care.

After the calculations conducted to one or more hidden layers of the MLP 820, information in the input layer of the MLP 820 may be transformed to an output layer of the MLP 820 (e.g., the right-most layer in the MLP 820 shown in FIG. 8). Based on the information in the output layer of the MLP 820, an output 805 may be generated. The output 805 may indicate the dementia subtype corresponding to the one or more input images (e.g., the GM image 203 and the CSF image 205). For example, the output 805 may indicate if the determined dementia subtype is vascular dementia (VaD), Alzheimer's disease (or Alzheimer's dementia) (AD), dementia with Lewy bodies (DLB), or frontotemporal dementia (FTD).

The CNN 810 and the MLP 820 may be trained based on a plurality of known cases. For example, in each known case, the input GM image 203 and the input CSF image 205, and the corresponding dementia subtype are known. The CNN 810 and the MLP 820 may be trained through a backpropagation method. That is, the parameters of the CNN 810 and the MLP 820 may be adjusted and updated through a backpropagation method.

Figure 9A:
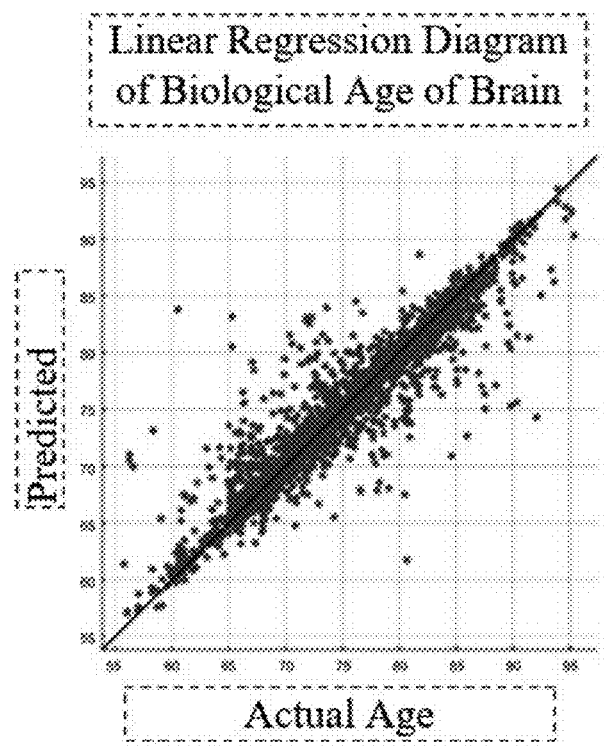
FIGS. 9A to 9D illustrate diagrams of performance according to some embodiments of the present disclosure.

FIGS. 9A to 9D illustrate diagrams of performance according to some embodiments of the present disclosure. FIG. 9A illustrates the linear regression diagram of biological age of brain. The x-axis of FIG. 9A indicates the actual age. The y-axis of FIG. 9A indicates the predicted age. The prediction error (i.e., the root-mean-square error) from FIG. 9A is 2.99 years. FIG. 9A shows that, for the same subject/patient, the predicted brain images for a given age and the actual brain images for the same given age are very similar.

Figure 9B:
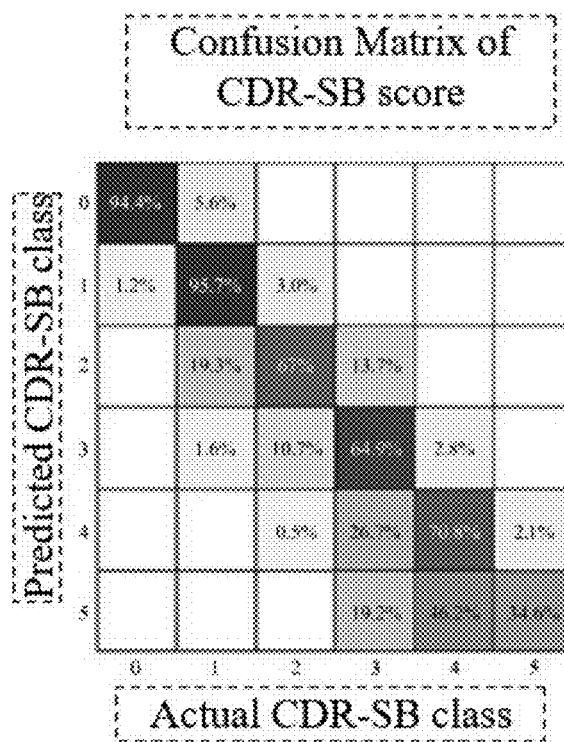

FIG. 9B illustrates the confusion matrix of CDR-SB score. The x-axis of FIG. 9B indicates the actual CDR-SB class. The y-axis of FIG. 9B indicates the predicted CDR-SB class. The accuracy from FIG. 9B is 89.7%. FIG. 9B shows that, for the same subject/patient, the predicted CDR-SB score and the actual CDR-SB score are very similar.

Figure 9C:
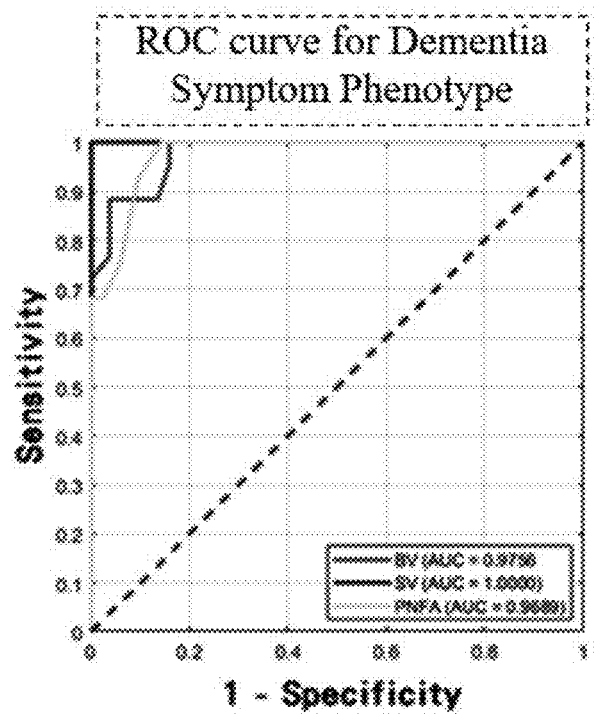

FIG. 9C illustrates the receiver operating characteristic (ROC) curve for dementia symptom phenotype. The x-axis of FIG. 9C indicates the sensitivity or the true positive rate. The y-axis of FIG. 9C indicates 1 minus the specificity or 1 minus the true negative rate. The term "BV" indicates "behavioral variant." The term "SV" indicates "semantic variant." The term "PNFA" indicates "progressive non fluent aphasia." The area under the curve (AUC) may be used to determine the accuracy of the predictor or the classifier. For example, if the AUC equals 1, the predictor (or the classifier) is perfect, and every prediction is correct. In FIG. 9C, for "BV," the AUC is 0.9756; for "SV" the AUC is 1; for "PNFA," the AUC is 0.9689. From FIG. 9C, the prediction performance for dementia symptom phenotype of the present disclosure is very good.

Figure 9D:
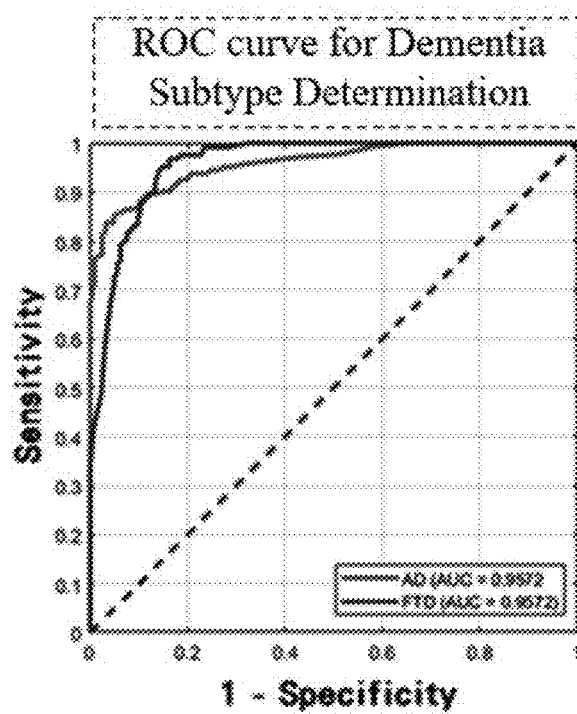

FIG. 9D illustrates the ROC curve for dementia subtype determination. The x-axis of FIG. 9C indicates the sensitivity or the true positive rate. The y-axis of FIG. 9C indicates 1 minus the specificity or 1 minus the true negative rate. In FIG. 9D, for subtype AD, the AUC is 0.9572; and for FTD, the AUC is 0.9572. From FIG. 9D, the prediction performance for dementia subtype of the present disclosure is very good.

Figure 10:
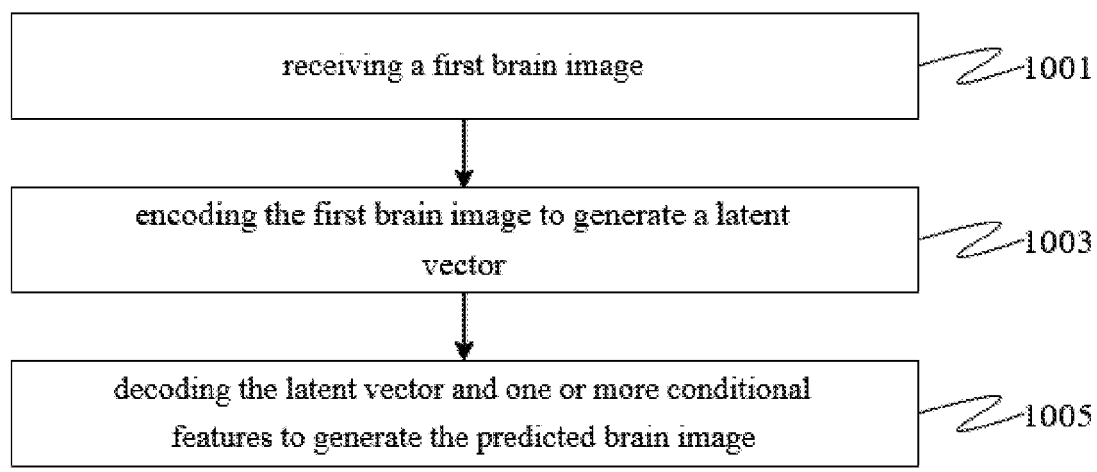
FIG. 10 is a flowchart of a method according to some embodiments of the present disclosure.

FIG. 10 is a flowchart of a method 1000 according to some embodiments of the present disclosure. The method 1000 may be a method of generating a predicted brain image. The method 1000 includes operations 1001, 1003, and 1005. In operation 1001, a first brain image may be received. The first brain image may be generated by the MRI method. In some embodiments, the first brain image may be generated by an 18 FDG-PET method or a PET method.

In operation 1003, the first brain image may be encoded. The first brain image may be encoded to generate a latent vector. The latent vector may be a low-dimensional vector. The latent vector may be multiplied with a normal distribution.

In operation 1005, the latent vector and one or more conditional features may be combined together. The latent vector and one or more conditional features are decoded together to generate the predicted brain image. The one or more conditional features may include at least one of: an age in future, a gender, previous brain images, omics features, and medical history.

Figure 11:
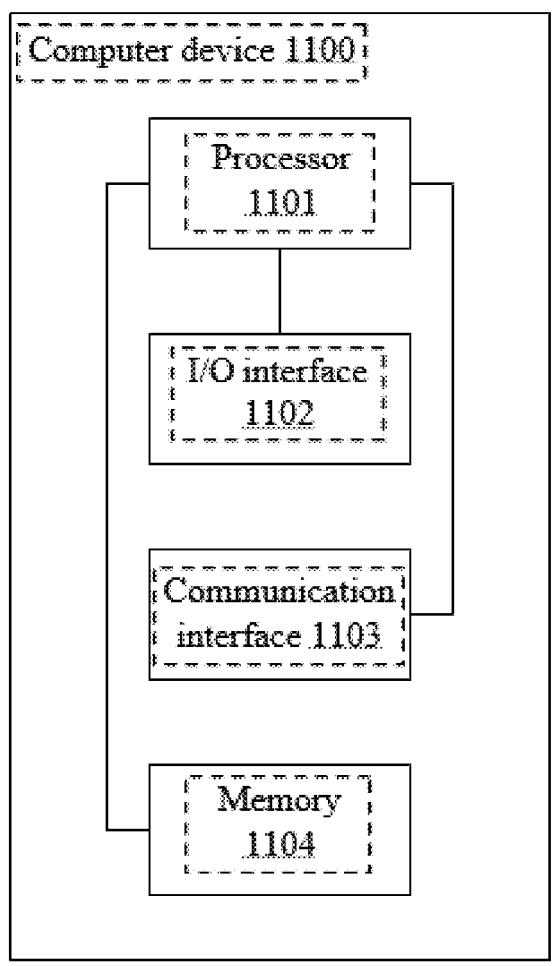
FIG. 11 illustrates a schematic diagram showing a computer device according to some embodiments of the present disclosure.

FIG. 11 illustrates a schematic diagram showing a computer device 1100 according to some embodiments of the present disclosure. The computer device 1100 may be capable of performing one or more procedures, operations, or methods of the present disclosure. The computer device 1100 may be a server computer, a client computer, a personal computer (PC), a tablet PC, a set-top box (STB), a personal digital assistant (PDA), a cellular telephone, or a smartphone. The computing device 1100 comprises processor 1101, input/output interface 1102, communication interface 1103, and memory 1104. The input/output interface 1102 is coupled with the processor 1101. The input/output interface 1102 allows the user to manipulate the computing device 1100 to perform the procedures, operations, or methods of the present disclosure (e.g., the procedures, operations, or methods disclosed in FIGS. 1-4, 7, 8, and 10). The communication interface 1103 is coupled with the processor 1101. The communication interface 1103 allows the computing device 1100 to communicate with data outside the computing device 1100, for example, receiving data including images or conditional features. A memory 1104 may be a non-transitory computer readable storage medium. The memory 1104 is coupled with the processor 1101. The memory 1104 has stored program instructions that can be executed by one or more processors (for example, the processor 1101). Upon execution of the program instructions stored on the memory 1104, the program instructions cause performance of the one or more procedures, operations, or methods disclosed in the present disclosure. For example, the program instructions may cause the computing device 1100 to perform, for example, receiving a first brain image; encoding the first brain image to generate a latent vector by the processor 1101; and decoding the latent vector and one or more conditional features to generate the predicted brain image by the processor 1101.

The scope of the present disclosure is not intended to be limited to the particular embodiments of the process, machine, manufacture, and composition of matter, means, methods, steps, and operations described in the specification. As those skilled in the art will readily appreciate from the disclosure of the present disclosure, processes, machines, manufacture, composition of matter, means, methods, steps, or operations presently existing or later to be developed that perform substantially the same function or achieve substantially the same result as the corresponding embodiments described herein may be utilized according to the present disclosure. Accordingly, the appended claims are intended to include within their scope processes, machines, manufacture, and compositions of matter, means, methods, steps, or operations. In addition, each claim constitutes a separate embodiment, and the combination of various claims and embodiments are within the scope of the disclosure.

The methods, processes, or operations according to embodiments of the present disclosure can also be implemented on a programmed processor. However, the controllers, flowcharts, and modules may also be implemented on a general purpose or special purpose computer, a programmed microprocessor or microcontroller and peripheral integrated circuit elements, an integrated circuit, a hardware electronic or logic circuit such as a discrete element circuit, a programmable logic device, or the like. In general, any device on which resides a finite state machine capable of implementing the flowcharts shown in the figures may be used to implement the processor functions of the present disclosure.

An alternative embodiment preferably implements the methods, processes, or operations according to embodiments of the present disclosure on a non-transitory, computer-readable storage medium storing computer programmable instructions. The instructions are preferably executed by computer-executable components preferably integrated with a network security system. The non-transitory, computer-readable storage medium may be stored on any suitable computer readable media such as RAMs, ROMs, flash memory, EEPROMs, optical storage devices (CD or DVD), hard drives, floppy drives, or any suitable device. The computer-executable component is preferably a processor, but the instructions may alternatively or additionally be executed by any suitable dedicated hardware device. For example, an embodiment of the present disclosure provides a non-transitory, computer-readable storage medium having computer programmable instructions stored therein.

While the present disclosure has been described with specific embodiments thereof, it is evident that many alternatives, modifications, and variations may be apparent to those skilled in the art. For example, various components of the embodiments may be interchanged, added, or substituted in the other embodiments. Also, all of the elements of each figure are not necessary for operation of the disclosed embodiments. For example, one of ordinary skill in the art of the disclosed embodiments would be able to make and use the teachings of the present disclosure by simply employing the elements of the independent claims. Accordingly, embodiments of the present disclosure as set forth herein are intended to be illustrative, not limiting. Various changes may be made without departing from the spirit and scope of the present disclosure.

Even though numerous characteristics and advantages of the present disclosure have been set forth in the foregoing description, together with details of the structure and function of the invention, the disclosure is illustrative only. Changes may be made to details, especially in matters of shape, size, and arrangement of parts, within the principles of the invention to the full extent indicated by the broad general meaning of the terms in which the appended claims are expressed.

What is claimed is:

1. A method of generating a predicted brain image, comprising:
   receiving a first brain image, the first brain image being generated by a magnetic resonance imaging (MRI) method;
   encoding the first brain image to generate a latent vector; and
   decoding the latent vector and one or more conditional features to generate the predicted brain image;
   calculating a reconstruction loss between the predicted brain image and a known brain image, wherein the predicted brain image and the known brain image are for a same age; and
   by a backpropagation method, adjusting encoding parameters and decoding parameters such that the reconstruction loss is minimized, the encoding parameters being used for encoding the first brain image and the decoding parameters being used for decoding the latent vector and the one or more conditional features,
   wherein the one or more conditional features include at least one of: an age in future, a gender, previous brain images, omics features, and medical history, and
   wherein the latent vector is multiplied by a first normal distribution.

2. The method of claim 1, further comprising:
   calculating a discriminate loss between the predicted brain image and a discriminate output of a discrimination procedure; and
   by a backpropagation method, adjusting decoding parameters such that the discriminate loss is maximized, the decoding parameters being used for decoding the latent vector and the one or more conditional features.

3. The method of claim 1, wherein the previous brain images include positron emission tomography (PET) images, and MRI images.

4. The method of claim 1, wherein the omics features include oral bacterial flora features, blood features, genomics features, and radiomics features.

5. The method of claim 4, wherein the genomics features include features associated with at least one of: ε4 allele of Apolipoprotein E (APOE) gene, tau proteins, granulin (GRN) gene, and C9ORF72 gene.

6. The method of claim 1, further comprising:
   determining a clinical dementia rating-sum of boxes (CDR-SB) score based on the predicted brain image.

7. The method of claim 6, further comprising:
   determining the CDR-SB score based on a gray matter segmentation and a cerebrospinal fluid (CSF) segmentation of the predicted brain image,
   wherein the gray matter segmentation and the CSF segmentation are encoded into a first vector by using a first modified ResNet, and
   the CDR-SB score is determined based one the first vector, the age in future, and the gender by using a first multilayer perceptron (MLP).

8. The method of claim 1, further comprising:
   determining a dementia subtype based on a gray matter segmentation and a cerebrospinal fluid (CSF) segmentation of the predicted brain image,
   wherein the gray matter segmentation and the CSF segmentation are encoded into a second vector by using a second modified ResNet, and the dementia subtype is determined based on the second vector, the omics features, and the medical history by using a second multilayer perceptron (MLP).

9. The method of claim 8, wherein the dementia subtype includes Alzheimer's disease (AD), vascular dementia (VaD), dementia with Lewy bodies (DLB), and frontotemporal dementia (FTD).

10. A device for generating a predicted brain image, comprising:
a processor; and
a memory coupled with the processor,
wherein the processor executes computer-readable instructions stored in the memory to perform operations, and the operations comprise:
receiving a first brain image, the first brain image being generated by a magnetic resonance imaging (MRI) method;
by means of the processor, encoding the first brain image to generate a latent vector; and
by means of the processor, decoding the latent vector and one or more conditional features to generate the predicted brain image;
by means of the processor, calculating a reconstruction loss between the predicted brain image and a known brain image, wherein the predicted brain image and the known brain image are for a same age; and
by means of the processor, adjusting encoding parameters through a backpropagation method such that the reconstruction loss is minimized, the encoding parameters being used for encoding the first brain image, and decoding parameters being used for decoding the latent vector and the one or more conditional features,
wherein the one or more conditional features include at least one of: an age in future, a gender, previous brain images, omics features, and medical history, and
wherein the latent vector is multiplied by a first normal distribution.

11. The device of claim 10, wherein the operations further comprise:
by means of the processor, calculating a discriminate loss between the predicted brain image and a discriminate output of a discrimination procedure; and
by means of the processor, adjusting decoding parameters through a backpropagation method such that the discriminate loss is maximized, the decoding parameters being used for decoding the latent vector and the one or more conditional features.

12. The device of claim 10, wherein the previous brain images include positron emission tomography (PET) images and MRI images.

13. The device of claim 10, wherein the omics features include oral bacterial flora features, blood features, genomics features, and radiomics features.

14. The device of claim 13, wherein the genomics features includes features associated with at least one of: ε4 allele of Apolipoprotein E (APOE) gene, tau proteins, granulin (GRN) gene, and C9ORF72 gene.

15. The device of claim 10, wherein the operations further comprise:
by means of the processor, determining a clinical dementia rating-sum of boxes (CDR-SB) score based on the predicted brain image.

16. The device of claim 15, wherein the operations further comprise:
by means of the processor, determining the CDR-SB score based on a gray matter segmentation and a cerebrospinal fluid (CSF) segmentation of the predicted brain image,
wherein the gray matter segmentation and the CSF segmentation are encoded into a first vector by using a first modified ResNet, and
the CDR-SB score is determined based one the first vector, the age in future, and the gender by using a first multilayer perceptron (MLP).

17. The device of claim 10, wherein the operations further comprise:
by means of the processor, determining a dementia subtype based on a gray matter segmentation and a cerebrospinal fluid (CSF) segmentation of the predicted brain image,
wherein the gray matter segmentation and the CSF segmentation are encoded into a second vector by using a second modified ResNet, and
the dementia subtype is determined based on the second vector, the omics features, and the medical history by using a second multilayer perceptron (MLP).

18. The device of claim 17, wherein the dementia subtype includes Alzheimer's disease (AD), vascular dementia (VaD), dementia with Lewy bodies (DLB), and frontotemporal dementia (FTD).

* * * * *